United States Patent [19]
Khan et al.

[11] Patent Number: 5,928,258
[45] Date of Patent: Jul. 27, 1999

[54] METHOD AND APPARATUS FOR LOADING A STENT OR STENT-GRAFT INTO A DELIVERY SHEATH

[75] Inventors: I. John Khan; Leonard Pinchuk; John B. Martin, Jr., all of Miami, Fla.

[73] Assignee: Corvita Corporation, Miami, Fla.

[21] Appl. No.: 08/947,450

[22] Filed: Sep. 26, 1997

[51] Int. Cl.$^6$ .................................................. A61B 17/00
[52] U.S. Cl. .......................................................... 606/191
[58] Field of Search ................................. 606/194, 198, 606/108, 151, 191, 192; 623/1, 11, 12

[56] References Cited

U.S. PATENT DOCUMENTS

| | | | |
|---|---|---|---|
| 3,585,707 | 6/1971 | Stevens | 29/427 |
| 4,921,484 | 5/1990 | Hillstead | 606/194 |
| 5,312,415 | 5/1994 | Palermo | 606/108 |
| 5,382,260 | 1/1995 | Dormandy, Jr. et al. | 606/151 |
| 5,458,615 | 10/1995 | Klemm et al. | 606/198 |
| 5,476,472 | 12/1995 | Dormandy, Jr. et al. | 606/151 |
| 5,603,698 | 2/1997 | Roberts et al. | 606/198 |
| 5,630,830 | 5/1997 | Verbeek | 606/198 |
| 5,776,140 | 7/1998 | Cottone | 606/198 |
| 5,776,141 | 7/1998 | Klein et al. | 606/198 |
| 5,776,142 | 7/1998 | Gunderson | 606/198 |
| 5,782,855 | 7/1998 | Lau et al. | 606/198 |

*Primary Examiner*—Michael Buiz
*Assistant Examiner*—Vikki Trinh
*Attorney, Agent, or Firm*—David P. Gordon; David S. Jacobson; Thomas A. Gallagher

[57] ABSTRACT

An apparatus for loading a self-expanding prosthesis into a delivery sheath includes a substantially cylindrical cartridge for receiving the prosthesis and a cartridge un-loading device for removing the prosthesis from the cartridge and loading it into a delivery sheath. The cartridge is provided with an exterior radial key at one end. The unloading device includes a substantially cylindrical member having an interior stationary coaxial piston extending substantially its entire length and an exterior sliding ring. The cylindrical member is provided with a radial slot which restricts movement of the sliding ring, and a stepped internal stop at one end. The stepped internal stop has a radial keyway which is dimensioned to receive the key on the cartridge. The sliding ring is provided with a radial pin which resides in the radial slot in the cylindrical member and which couples the sliding ring to an interior key engaging member with a locking keyway dimensioned to engage the key on the cartridge. The method of the invention includes loading the prosthesis into the cartridge, attaching the cartridge to the unloading device, placing the delivery sheath over the cartridge, and pulling the cartridge into the unloading device leaving the prosthesis inside the delivery sheath.

19 Claims, 6 Drawing Sheets

METHOD AND APPARATUS FOR LOADING A STENT OR STENT-GRAFT INTO A DELIVERY SHEATH

This application is related to co-owned U.S. Pat. No. 5,632,772 and co-owned U.S. Pat. No. 5,628,788.

BACKGROUND OF THE INVENTION

1. Field of the Invention

The invention relates to implantable prostheses. In particular, the invention relates to endoluminal stents and stent-grafts which are deployed in a blood vessel with the use of a delivery sheath. More particularly, the invention is related to a method and apparatus for loading the prosthesis into a delivery sheath.

2. State of the Art

An endoluminal stent-graft typically includes tubular graft material which is affixed to the inside or outside of a woven metallic stent. Endoluminal stent-grafts are most often used to repair blood vessels affected by a variety of lesions such as stenoses or aneurysms. The stent-graft is delivered to the damaged site of a blood vessel and is deployed using an introducer which tracks on a guide wire. The introducer preferably includes a delivery sheath and a plunger catheter. The stent-graft is placed in the delivery sheath where it is held in a radially compressed state. The introducer is delivered over the guide wire to the deployment site. With the sheath in position, the plunger catheter is used to push the stent-graft out of the sheath, whereupon the stent-graft self-expands.

Figure 1:
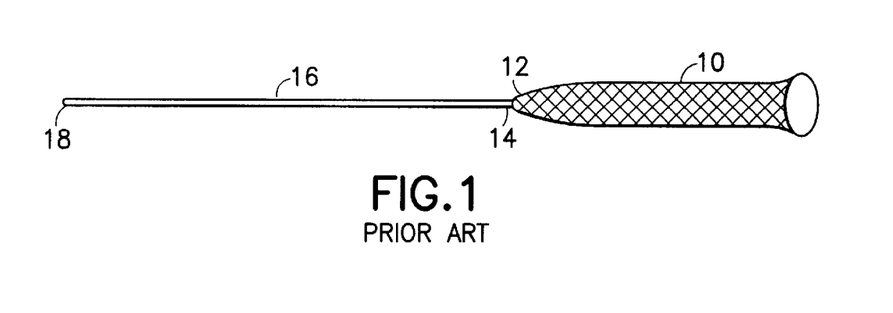
FIGS. 1–3 are schematic perspective views illustrating a presently known method and apparatus for loading a self-expanding prosthesis into a delivery sheath.
Figure 2:
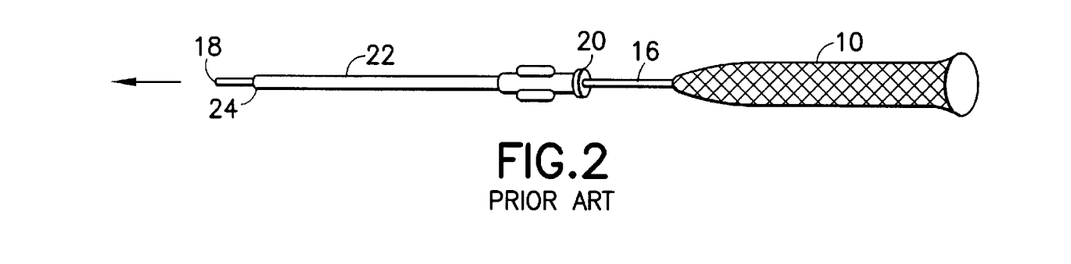
Figure 3:
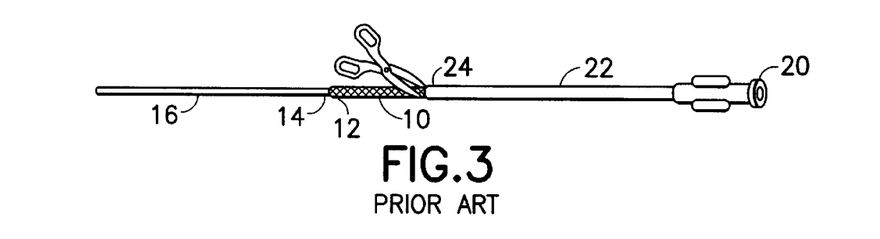
Figure 4:
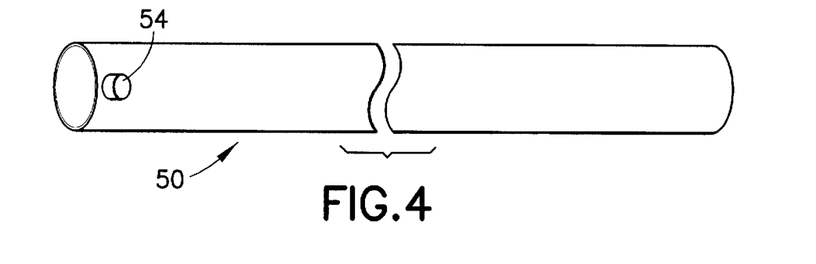
FIG. 4 is a broken perspective view of the cartridge portion of the apparatus of the invention.
Figure 5:
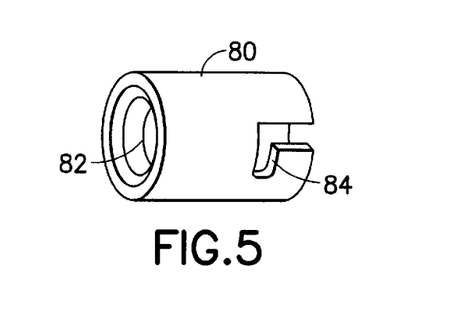
FIG. 5 is a perspective view of the removable tapered collar of the apparatus of the invention.
Figure 6:
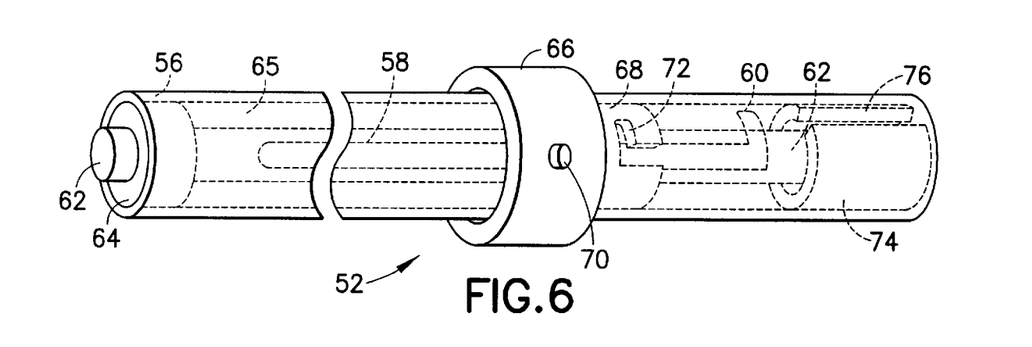
FIG. 6 is a broken perspective view of the unloading device of the apparatus of the invention.
Figure 7:
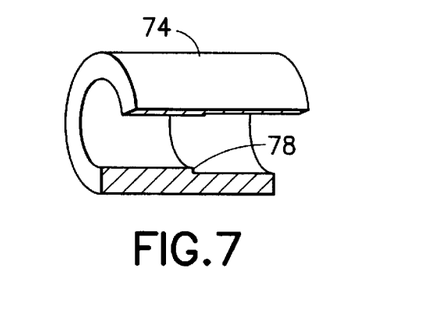
FIG. 7 is a cut away perspective view of the stepped collar of the unloading device of FIG. 6.
Figure 8:
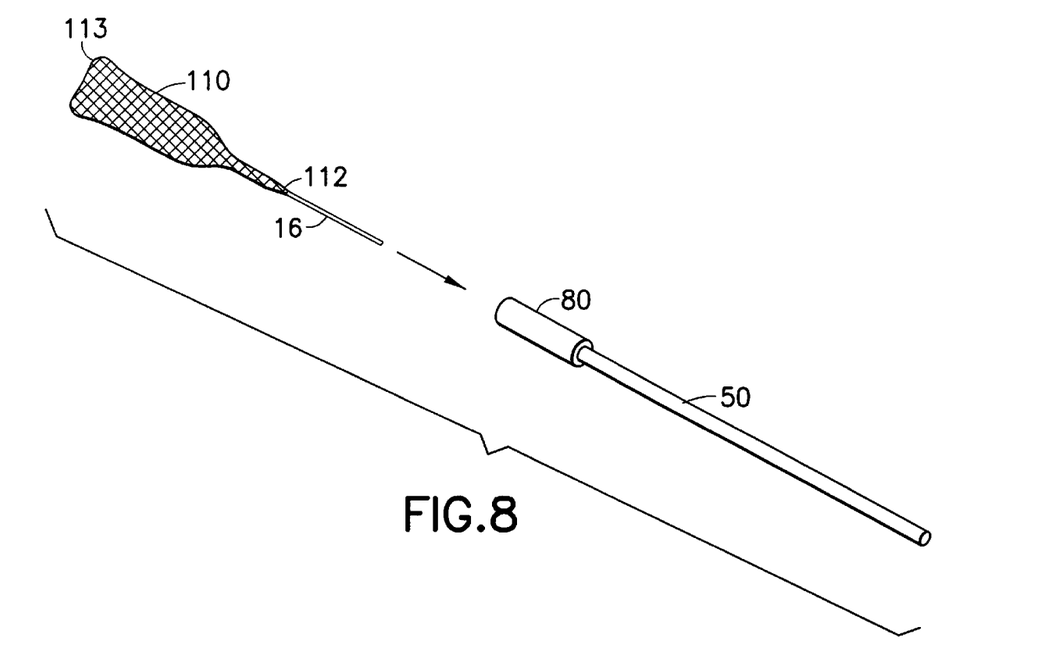
FIGS. 8–16 are schematic perspective views illustrating the method of the invention.

Various methods and apparatus are used to load the stent-graft into the delivery sheath. One known method and apparatus for loading the delivery sheath was developed by one of the inventors herein and is shown in FIGS. 1–3. According to this method, a self-expanding stent-graft 10 is attached at one end 12 to one end 14 of a rod or tube 16 as shown in FIG. 1. The other end 18 of the rod 16 is inserted into the proximal end 20 of a delivery sheath 22 and pushed through the sheath until it exits the distal end 24 of the sheath 22 as shown in FIG. 2. The rod is pulled through the sheath 22 until the end 12 of the stent-graft 10 exits the distal end 24 of the sheath 22 as shown in FIG. 3, after which a measured length of the stent-graft 10 is cut leaving a measured length of the stent-graft 10 inside the sheath 22.

State-of-the-art stents and stent-grafts often have naturally flared ends which aid in the placement of the prosthesis and prevent the prosthesis from becoming dislodged or displaced after placement. In some cases, both ends of the stent are naturally flared. Ends which are naturally flared generally can be cut without adversely affecting the flare of the ends as the new end will take the same flare. Stents with naturally flared ends can be compressed to a non-flared state so they can be pushed through a delivery sheath without damaging the sheath or the ends of the stent. Some new stents and stent-grafts provided by the assignee hereof have at least one end which is "manually" flared (i.e. flared in a controlled manner by a specific manufacturing process). Stents of this type are disclosed in co-owned U.S. Pat. No. 5,632,772 and co-owned U.S. Pat. No. 5,628,788. The manually flared ends of these stents cannot be cut without losing the flare. In addition, these stents generally can only be pushed through a delivery sheath in one direction lest the sheath and/or the stent be damaged. It will be appreciated that the method and apparatus described above with reference to FIGS. 1–3 is not suitable for use with stents or stent-grafts which have a manually flared distal end as the orientation of the stent is important both for cutting and deployment purposes. As used herein, the "distal end" is used to refer to the end of the stent or stent-graft which is most distant from the practitioner and the term "proximal end" is used to refer to the end of the stent or stent-graft which is closest to the practitioner.

SUMMARY OF THE INVENTION

It is therefore an object of the invention to provide a method and apparatus for loading a stent or a stent-graft into a delivery sheath.

It is also an object of the invention to provide a method and apparatus for loading a stent or a stent-graft into a delivery sheath which can be used with a stent or stent-graft having a manually flared distal end.

It is another object of the invention to provide a method and apparatus for loading a stent or a stent-graft into a delivery sheath which does not damage the stent or stent-graft.

It is still another object of the invention to provide a method and apparatus for loading a stent or a stent-graft into a delivery sheath which does not damage the delivery sheath.

In accord with these objects which will be discussed in detail below, the apparatus of the present invention includes a substantially cylindrical cartridge for receiving a stent or stent graft and a cartridge unloading device for removing a stent or stent-graft from the cartridge and-loading it into a delivery sheath. The cartridge is long enough to accommodate a radially contracted stent-graft, has an outer diameter small enough to fit inside a delivery sheath, and is provided with an exterior radial key at one end. The unloading device includes a substantially cylindrical member having an interior stationary coaxial piston extending substantially its entire length and an exterior sliding ring. The cylindrical member is provided with a radial slot which restricts movement of the sliding ring, and a stepped internal stop at one end. The stepped internal stop has a radial keyway which is dimensioned to receive the key on the cartridge. The sliding ring is provided with a radial pin which resides in the radial slot in the cylindrical member and which couples the sliding ring to an interior key engaging member with a locking keyway dimensioned to engage the key on the cartridge. The apparatus also preferably includes a removable collar having a tapered interior and a locking keyway which is attachable to the cartridge.

The method of the invention includes the following steps: The removable collar is attached to the cartridge to provide a tapered access to the interior of the cartridge. The proximal end of a stent or stent-graft having a manually flared distal end is attached to a rod or tube which is inserted into the removable collar. The rod or tube is pulled through the cartridge until the proximal end of the prosthesis exits the end of the cartridge opposite the end carrying the collar. The proximal end of the prosthesis is cut to a measured length leaving a measured length of the prosthesis including the manually flared distal end of the stent inside the cartridge. The sliding ring of the unloading device is moved toward the stepped internal stop and is rotated so that the key engaging member is aligned with the keyway in the stepped internal stop. The tapered collar is removed from the cartridge and the keyed end of the cartridge is inserted into the stepped internal stop of the unloading device and into the key engaging member. The cartridge is rotated until the key engages the locking keyway of the interior key engaging member. A delivery sheath is then slid over the cartridge until the distal end of the delivery sheath enters the stepped internal stop of the unloading device. The sliding ring is rotated and pulled away from the internal stop, carrying the cartridge with it into the cylindrical member of the unloading device. The coaxial stationary piston prevents the prosthesis from entering the unloading device and the prosthesis remains inside the delivery sheath after the cartridge is removed from the delivery sheath. The delivery sheath is then removed from the apparatus. The delivery sheath now has the prosthesis loaded inside it with the manually flared distal end of the prosthesis adjacent the distal end of the sheath. The prosthesis may now be deployed in a body in a conventional manner.

Additional objects and advantages of the invention will become apparent to those skilled in the art upon reference to the detailed description taken in conjunction with the provided figures.

DETAILED DESCRIPTION OF THE PREFERRED EMBODIMENTS

Referring now to FIGS. 4 through 7, the apparatus of the present invention includes a substantially cylindrical cartridge 50 and a cartridge unloading device 52. The cartridge 50 is long enough to accommodate a radially contracted stent-graft, has an outer diameter small enough to fit inside a delivery sheath, and is provided with an exterior radial key 54 at one end. The unloading device 52 includes a substantially cylindrical member 56. The cylindrical member 56 has a radial slot 58 which extends along substantially the entire length of the member 56 and has an orthogonal bend 60 at its forward end. An interior coaxial piston 62 is located inside the cylindrical member 56 and is held stationary by an annular stop 64 in the rearward end of the member 56. The piston 62 defines an annular space 65 inside the cylindrical member 56. An exterior sliding ring 66 is mounted on the cylindrical member 56 and is coupled to an interior key engaging member 68 with a screw 70 which extends through the slot 58. The key engaging member 68 is provided with a locking keyway 72 which is dimensioned to receive the key 54 of the cartridge 50. A stepped interior forward stop 74 is provided in the forward end of the cylindrical member 56. The stop 74 has a keyway 76 which is dimensioned to allow passage of the key 54 on the cartridge 50 and an interior step 78 (FIG. 7) which is dimensioned to block passage of a delivery sheath as shown and described below. The step 78 is preferably aligned with the forward end of the piston 62. The apparatus of the invention also preferably includes a removable collar 80 (FIG. 5) having a tapered interior 82 and a locking keyway 84. The collar 80 is attachable to the cartridge 50 as described below.

Figure 9:
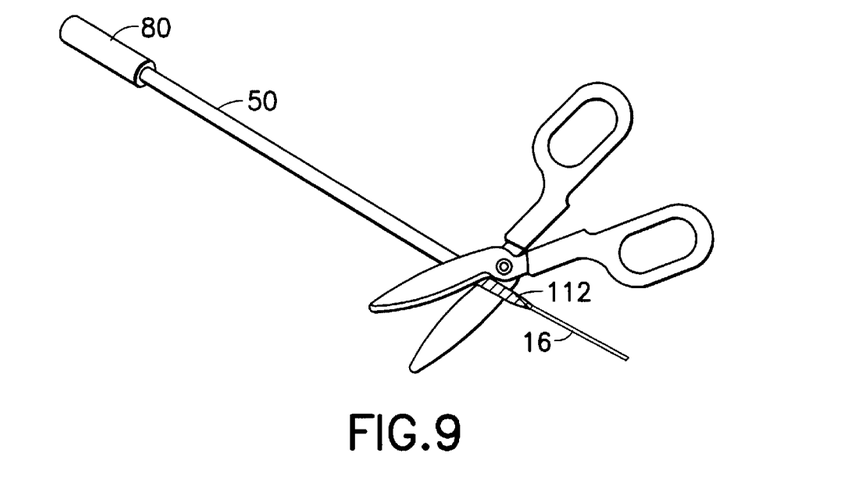

Turning now to FIGS. 8–16 and with reference to FIGS. 4–7, the method of the invention includes the following steps. The removable collar 80 is attached to the cartridge to provide a tapered access to the interior of the cartridge 50. The proximal end 112 of a stent or stent-graft 110 having a manually flared distal end 113 is attached to a rod or tube 16. The tube 16 is inserted into the removable collar 80 as indicated by the arrow in FIG. 8. The rod or tube 16 is pulled through the cartridge 50 until the proximal end 112 of the prosthesis exits the end of the cartridge opposite the end carrying the collar 80. The proximal end 112 of the prosthesis is cut leaving a measured length of the prosthesis including the manually flared distal end of the stent inside the cartridge 50 as shown in FIG. 9.

Figure 10:
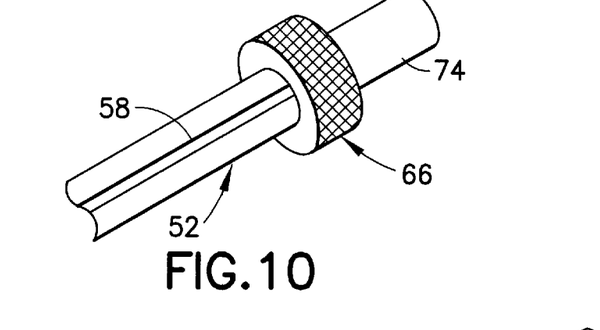
Figures 11, 12:
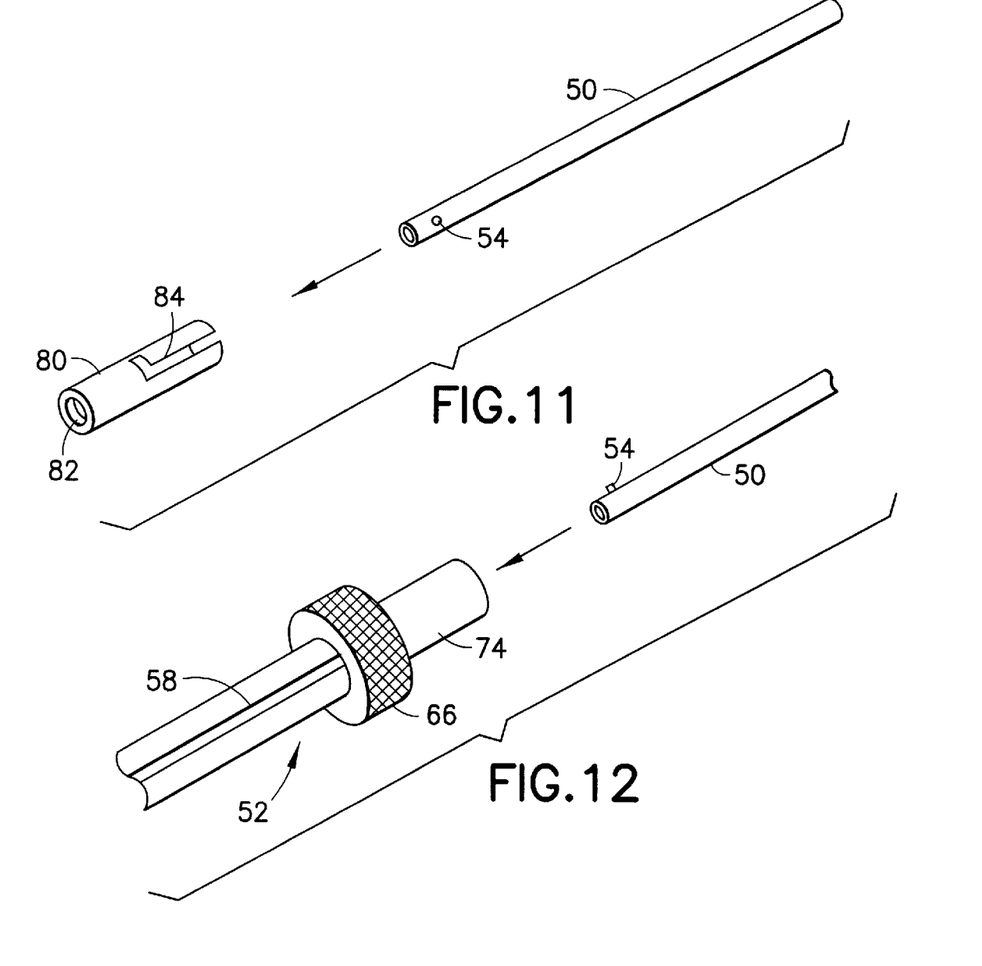
Figure 13:
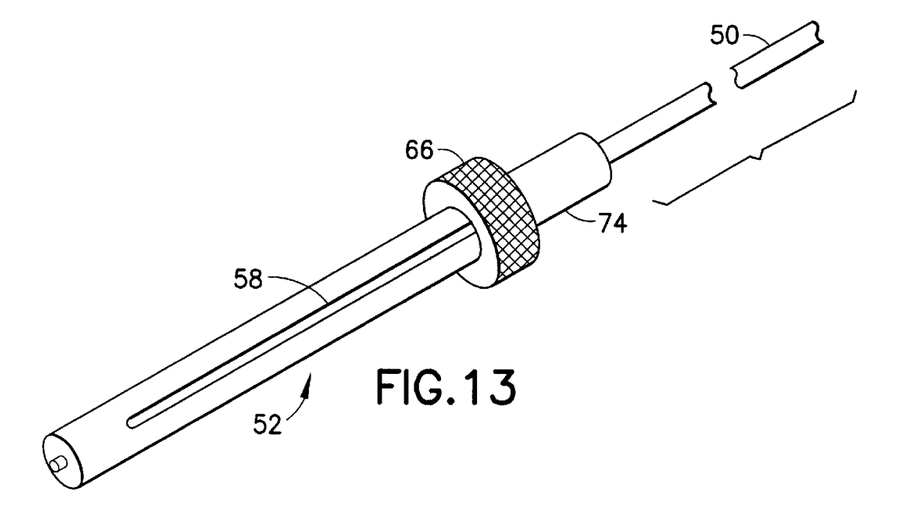

The sliding ring 66 of the unloading device 52 is moved toward the stepped internal stop 74 as shown in FIG. 10 and is rotated so that locking keyway 72 (see FIG. 6) of the interior key engaging member 68 is aligned with the keyway 76 in the stepped internal stop 74. This also locks the axial position of the sliding ring because the screw 70 is located in the bend 60 of the slot 58 when the key engaging member 68 is aligned with the keyway 76 in the stepped internal stop 74. The tapered collar 80 is removed from the cartridge 50 as shown in FIG. 11 and the keyed end of the cartridge 50 is inserted through the stepped internal stop 74 of the unloading device 52 and into the key engaging member 68 as shown in FIGS. 12 and 13. The cartridge 50 is rotated until the key 54 engages the locking keyway 72 (see FIG. 6) of the interior key engaging member 68.

Figure 14:
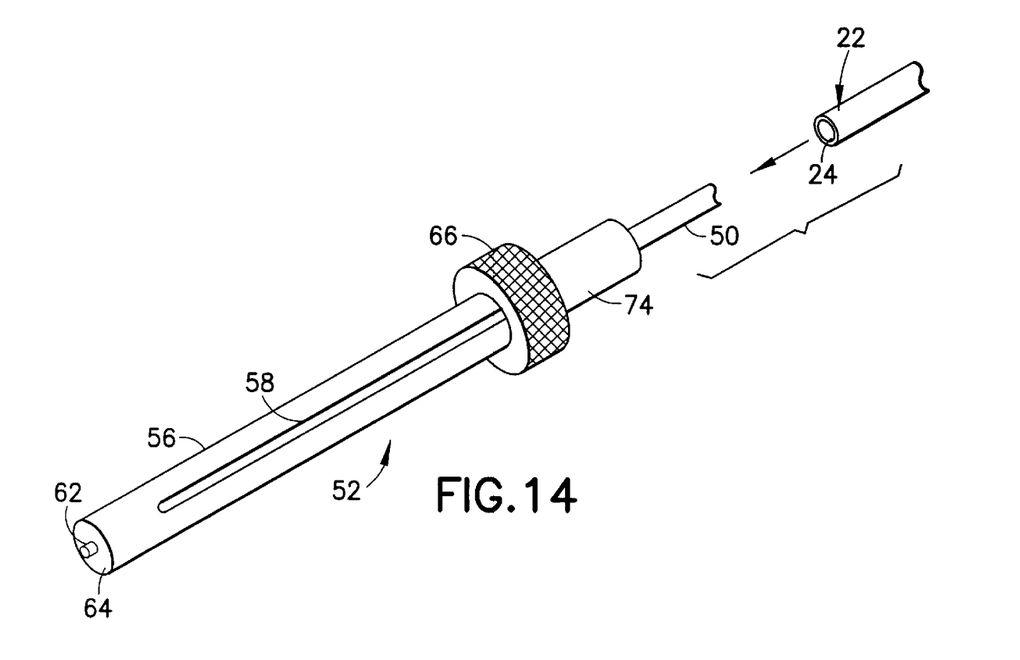
Figure 15:
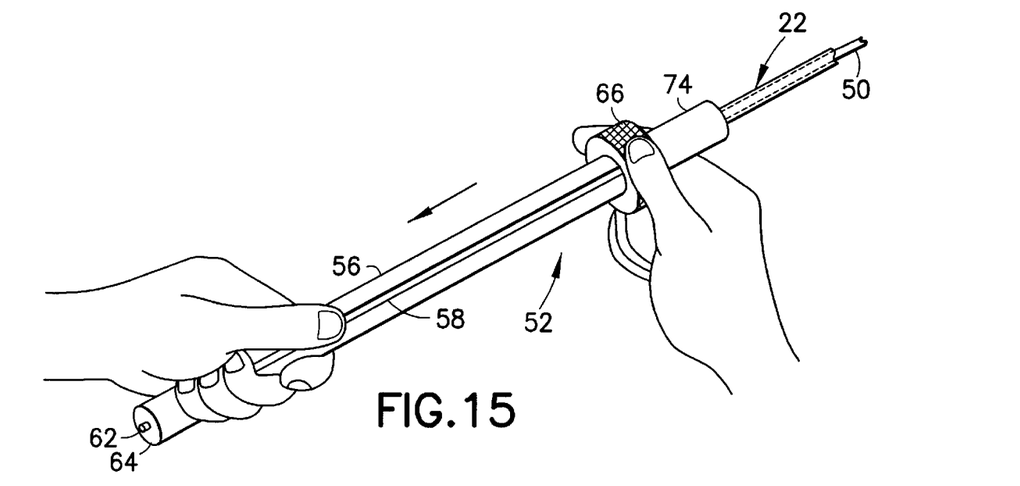

A delivery sheath 22 is slid over the cartridge 50 as shown in FIG. 14 until the distal end 24 of the delivery sheath 22 enters the stepped internal stop 74 of the unloading device 52 and is stopped by the step 78 (see FIG. 7) of the stop 74. The sliding ring 66 is rotated as shown in FIG. 15 so that the screw 70 (see FIG. 6) no longer resides in the bend 60 of the slot 58. The sliding ring 66 is then pulled away from the internal stop 74, as indicated by the arrow in FIG. 15, carrying the cartridge 50 with it into the annular space 65 in the cylindrical member 56 of the unloading device 52. The coaxial stationary piston 62 prevents the prosthesis from entering the unloading device and the prosthesis remains inside the delivery sheath 22 after the cartridge 50 is removed from the delivery sheath 22. The delivery sheath 22 is then removed from the apparatus as shown by the arrow in FIG. 16.

Figure 16:
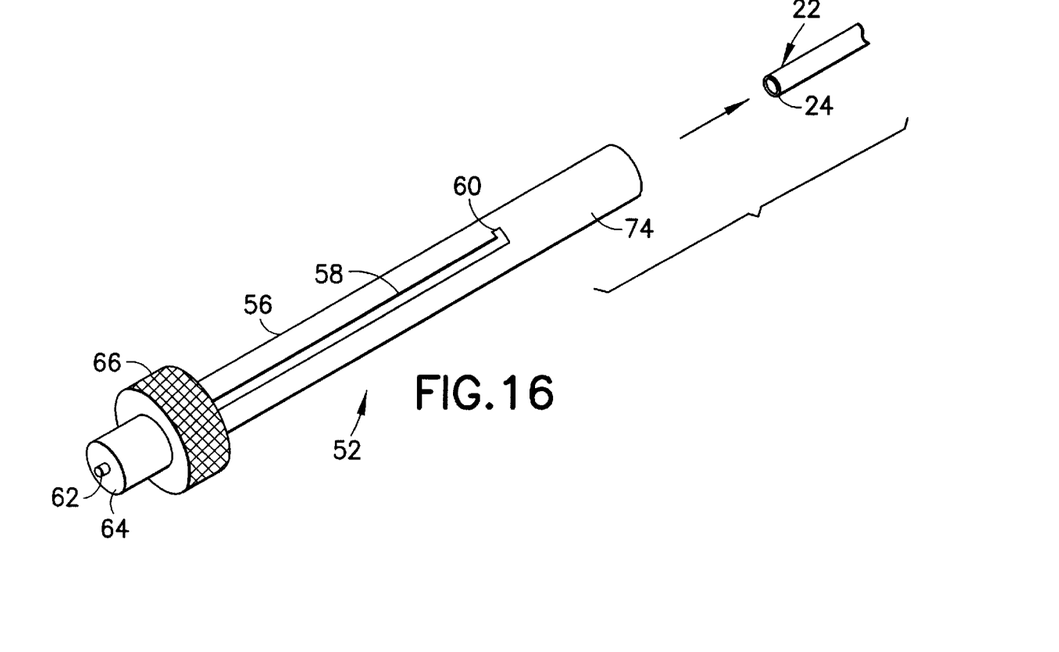

The delivery sheath now has the prosthesis loaded inside it with the manually flared distal end of the prosthesis adjacent the distal end 24 of the sheath 22. The prosthesis may now be deployed in a conventional manner.

There have been described and illustrated herein a method and apparatus for loading a self-expanding prosthesis into a delivery sheath. While particular embodiments of the invention have been described, it is not intended that the invention be limited thereto, as it is intended that the invention be as broad in scope as the art will allow and that the specification be read likewise. Thus, while particular means have been shown for attaching the cartridge to the collar and the sliding ring have been disclosed, it will be appreciated that other connectors such as threaded connectors or snap connectors could be utilized. Also, while a sliding ring has been shown for moving the cartridge into the unloading device, it will be recognized that other types of slidable structures could be used with similar results obtained. For example, a radial pin attached to the engaging member would be effective. In addition, the key on the cartridge could be used to move the cartridge if it were lengthened slightly and the slot in the unloading device were continued to the forward end of the device. Moreover, while particular configurations have been disclosed in reference to the stationary piston, it will be appreciated that other configurations could be used as well. The essence of the stationary piston is to prevent the prostheses from being carried with the cartridge into the unloading device. It will therefore be appreciated by those skilled in the art that yet other modifications could be made to the provided invention without deviating from its spirit and scope as so claimed.

We claim:

1. An apparatus for loading a self-expanding prosthesis into a delivery sheath, comprising:

a) a first hollow substantially cylindrical means for releasably receiving and temporarily holding substantially all of the prosthesis prior to loading into the delivery sheath, said first substantially cylindrical means being dimensioned to fit inside the delivery sheath;

b) a second substantially cylindrical member having means for receiving substantially all of said first substantially cylindrical means and means for preventing the prosthesis temporarily held in said first substantially cylindrical means from being received by said second substantially cylindrical member, such that when the delivery sheath is placed over said first substantially cylindrical means and said first substantially cylindrical means is received by said second substantially cylindrical member, said means for preventing thereby causes the prosthesis to be released from said first substantially cylindrical means into the delivery sheath.

2. An apparatus according to claim 1, further comprising:

c) a removable collar attachable to said first substantially cylindrical means, said removable collar having a tapered interior for facilitating entry of the prosthesis into said first substantially cylindrical means.

3. An apparatus according to claim 1, wherein:

said means for preventing includes a piston disposed inside said second substantially cylindrical member, and said means for receiving said first second substantially cylindrical means includes an annular space between said piston and said second substantially cylindrical member.

4. An apparatus according to claim 1, further comprising:

c) means for moving said first substantially cylindrical means into said second substantially cylindrical member.

5. An apparatus according to claim 4, wherein:

said means for moving includes means for coupling said first substantially cylindrical means to said means for moving.

6. An apparatus according to claim 5, wherein:

said second substantially cylindrical member includes a radial slot, said means for moving includes a portion located inside said second substantially cylindrical member and a portion extending through said radial slot.

7. An apparatus according to claim 6, wherein:

said radial slot has a substantially orthogonal bend at one end thereof.

8. An apparatus according to claim 1, wherein:

said second substantially cylindrical member has means for preventing a delivery sheath from being received by said second substantially cylindrical member.

9. An apparatus according to claim 8, wherein:

said means for preventing a delivery sheath from being received by said second substantially cylindrical member includes an annular step.

10. A method for loading a self-expanding prosthesis into a delivery sheath, comprising:

a) loading the prosthesis into a first cylindrical member;

b) placing the delivery sheath over the first cylindrical member;

c) placing an obstructing member at a first end of the first cylindrical member; and d) moving the first end of the first cylindrical member over the obstructing member such that the first cylindrical member exits the sheath leaving the prosthesis inside the sheath.

11. A method according to claim 10, wherein:

said step of loading the prosthesis into the first cylindrical member includes attaching one end of the prosthesis to a rod and inserting the rod into the first cylindrical member.

12. A method according to claim 11, wherein:

said step of loading the prosthesis into the first cylindrical member includes detaching the rod from the prosthesis after the prosthesis is inside the first cylindrical member.

13. A method according to claim 12, wherein:

said step of detaching includes cutting the prosthesis.

14. A method according to claim 10, wherein:

said step of placing an obstructing member at a first end of the first cylindrical member includes placing a second cylindrical member with an interior obstructing member adjacent to the first end of the first cylindrical member, and said step of moving the first end of the first cylindrical member over the obstructing member includes moving the first cylindrical member into the second cylindrical member.

15. A method according to claim 14, wherein:

said step of moving includes attaching the first end of the first cylindrical member to a sliding member coupled to the second cylindrical member.

16. A method according to claim 10, wherein:

said step of loading the prosthesis into the first cylindrical member includes attaching a tapered collar to the first end of the first cylindrical member.

17. A method according to claim 16, wherein said step of loading the prosthesis into the first cylindrical member includes attaching one end of the prosthesis to a rod and inserting the rod into the first end of the first cylindrical member.

18. An apparatus for loading a self-expanding prosthesis into a delivery sheath, comprising:

a) a first hollow substantially cylindrical means for releasably receiving and temporarily holding substantially all of the prosthesis prior to loading into the delivery sheath, said first substantially cylindrical means being dimensioned to fit inside the delivery sheath and having a first coupling means at a first end thereof;

b) a second substantially cylindrical member having a coaxial stopping member defining an annular space dimensioned to receive substantially all of said first substantially cylindrical means but not the prosthesis; and c) a sliding member coupled to said second substantially cylindrical member and having second coupling means for coupling to said first coupling means, such that
  when the delivery sheath is placed over said first substantially cylindrical means and said first substantially cylindrical means is received by said second substantially cylindrical member, said stopping member thereby causes the prosthesis to be released from said first substantially cylindrical means into the delivery sheath.

19. An apparatus according to claim 18, further comprising:

d) means for receiving a distal end of the delivery sheath coupled to said second substantially cylindrical member, said means for receiving including means for preventing the delivery sheath from entering substantially into said annular space.

\* \* \* \* \*